United States Patent
Mauch et al.

(10) Patent No.: US 8,916,226 B2
(45) Date of Patent: Dec. 23, 2014

(54) METHOD OF FORMING HOLLOW TUBULAR DRUG ELUTING MEDICAL DEVICES

(71) Applicants: Kevin Mauch, Windsor, CA (US); Sean Ward, County Louth (IE); Aram Jamous, Oranmore (IE)

(72) Inventors: Kevin Mauch, Windsor, CA (US); Sean Ward, County Louth (IE); Aram Jamous, Oranmore (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/038,300

(22) Filed: Sep. 26, 2013

(65) Prior Publication Data

US 2014/0091057 A1    Apr. 3, 2014

Related U.S. Application Data

(63) Continuation of application No. 12/884,551, filed on Sep. 17, 2010, now abandoned.

(60) Provisional application No. 61/244,049, filed on Sep. 20, 2009.

(51) Int. Cl.
| | | |
|---|---|---|
| B23P 13/04 | (2006.01) | |
| A61F 2/06 | (2013.01) | |
| A61L 33/00 | (2006.01) | |
| A61M 31/00 | (2006.01) | |
| A61F 2/88 | (2006.01) | |
| A61L 31/16 | (2006.01) | |

(52) U.S. Cl.
CPC ............... *A61M 31/002* (2013.01); *A61F 2/88* (2013.01); *A61L 31/16* (2013.01); *A61F 2240/001* (2013.01); *A61F 2250/0068* (2013.01); *A61F 2220/0041* (2013.01); *A61F 2220/005* (2013.01); *A61F 2220/0058* (2013.01); *A61F 2220/0075* (2013.01)
USPC ............ 427/2.1; 427/2.24; 427/2.25; 29/557; 623/1.15; 623/1.42

(58) Field of Classification Search
USPC .......................................... 29/557; 623/1.15
See application file for complete search history.

(56) References Cited

U.S. PATENT DOCUMENTS

| | | | |
|---|---|---|---|
| 2,153,936 A | 4/1939 | Owens et al. | |
| 3,626,759 A | 12/1971 | Ardon | |

(Continued)

FOREIGN PATENT DOCUMENTS

| | | |
|---|---|---|
| EP | 836839 A2 | 10/1997 |
| EP | 1600534 | 11/2005 |

(Continued)

OTHER PUBLICATIONS

U.S. Appl. No. 07/574,629, filed Aug. 29, 1990, Dhuwalia.

(Continued)

*Primary Examiner* — Cachet Sellman

(57) ABSTRACT

A method of a forming a hollow, drug-eluting medical device includes utilizing a hollow wire having an outer member and a lumen of the outer member, and filling the lumen with a fluid to form a supported hollow wire. The supported hollow wire is shaped into a stent pattern. Openings are formed through the outer member. The supported hollow wire is processed to remove the fluid from the lumen of the outer member without adversely affecting the outer member, leaving the hollow wire shaped into a stent pattern. The lumen is filled with a biologically or pharmacologically active substance.

13 Claims, 10 Drawing Sheets

(56) References Cited

U.S. PATENT DOCUMENTS

| | | | |
|---|---|---|---|
| 4,531,933 | A | 7/1985 | Norton et al. |
| 4,643,716 | A | 2/1987 | Drach |
| 4,720,384 | A | 1/1988 | DiLuccio et al. |
| 4,739,762 | A | 4/1988 | Palmaz |
| 4,763,647 | A | 8/1988 | Gambale |
| 4,800,882 | A | 1/1989 | Gianturco |
| 4,813,925 | A | 3/1989 | Anderson, Jr. |
| 4,886,062 | A | 12/1989 | Wiktor |
| 4,913,683 | A | 4/1990 | Gregory |
| 5,019,090 | A | 5/1991 | Pinchuk |
| 5,063,935 | A | 11/1991 | Gambale |
| 5,133,732 | A | 7/1992 | Wiktor |
| 5,154,705 | A | 10/1992 | Fleischhacker et al. |
| 5,234,456 | A | 8/1993 | Silvestrini |
| 5,292,331 | A | 3/1994 | Boneau |
| 5,306,250 | A | 4/1994 | March et al. |
| 5,327,764 | A | 7/1994 | Weykamp et al. |
| 5,345,945 | A | 9/1994 | Hodgson et al. |
| 5,421,955 | A | 6/1995 | Lau |
| 5,536,274 | A | 7/1996 | Neuss |
| 5,538,735 | A | 7/1996 | Ahn |
| 5,569,197 | A | 10/1996 | Helmus et al. |
| 5,605,162 | A | 2/1997 | Mirzaee et al. |
| 5,605,696 | A | 2/1997 | Eury et al. |
| 5,630,840 | A | 5/1997 | Mayer |
| 5,670,161 | A | 9/1997 | Healy et al. |
| 5,782,903 | A | 7/1998 | Wiktor |
| 5,795,318 | A | 8/1998 | Wang et al. |
| 5,824,045 | A | 10/1998 | Alt |
| 5,843,117 | A | 12/1998 | Alt et al. |
| 5,882,335 | A | 3/1999 | Leone et al. |
| 5,891,108 | A | 4/1999 | Leone et al. |
| 5,902,266 | A | 5/1999 | Leone et al. |
| 5,957,903 | A | 9/1999 | Mirzaee et al. |
| 6,022,369 | A | 2/2000 | Jacobsen et al. |
| 6,063,101 | A | 5/2000 | Jacobsen et al. |
| 6,071,305 | A | 6/2000 | Brown et al. |
| 6,090,127 | A | 7/2000 | Globerman |
| 6,099,561 | A | 8/2000 | Alt |
| 6,136,023 | A | 10/2000 | Boyle |
| 6,248,190 | B1 | 6/2001 | Stinson |
| 6,253,443 | B1 * | 7/2001 | Johnson ............... 29/557 |
| 6,290,721 | B1 | 9/2001 | Heath |
| 6,358,276 | B1 | 3/2002 | Edwin |
| 6,378,352 | B1 | 4/2002 | Bossard et al. |
| 6,379,383 | B1 | 4/2002 | Palmaz et al. |
| 6,425,855 | B2 | 7/2002 | Tomonto |
| 6,478,778 | B1 | 11/2002 | Jacobsen et al. |
| 6,497,709 | B1 | 12/2002 | Heath |
| 6,558,422 | B1 | 5/2003 | Baker et al. |
| 6,623,519 | B2 | 9/2003 | Edwin |
| 6,641,607 | B1 | 11/2003 | Hossainy et al. |
| 6,656,162 | B2 | 12/2003 | Santini, Jr. et al. |
| 6,699,281 | B2 | 3/2004 | Vallana et al. |
| 6,752,829 | B2 | 6/2004 | Kocur et al. |
| 6,758,859 | B1 * | 7/2004 | Dang et al. ............... 623/1.15 |
| 6,783,543 | B2 | 8/2004 | Jang |
| 6,849,085 | B2 | 2/2005 | Marton |
| 6,989,071 | B2 | 1/2006 | Kocur et al. |
| 7,041,130 | B2 | 5/2006 | Santini, Jr. et al. |
| 7,044,965 | B1 | 5/2006 | Spielberg |
| 7,060,093 | B2 | 6/2006 | Dang et al. |
| 7,101,392 | B2 | 9/2006 | Heath |
| 7,122,048 | B2 | 10/2006 | Dimatteo et al. |
| 7,135,039 | B2 | 11/2006 | De Scheerder et al. |
| 7,182,735 | B2 | 2/2007 | Shireman et al. |
| 7,288,084 | B2 | 10/2007 | Li |
| 7,305,860 | B2 | 12/2007 | Yang et al. |
| 7,316,565 | B2 | 1/2008 | Liao |
| 7,344,563 | B2 | 3/2008 | Vallana et al. |
| 7,384,660 | B2 | 6/2008 | Hossainy et al. |
| 7,400,931 | B2 | 7/2008 | Mandrusov et al. |
| 7,419,681 | B2 | 9/2008 | Tormala et al. |
| 7,455,667 | B2 | 11/2008 | Uhland et al. |
| 7,575,593 | B2 | 8/2009 | Rea et al. |
| 2002/0065548 | A1 | 5/2002 | Birdsall et al. |
| 2002/0087209 | A1 | 7/2002 | Edwin et al. |
| 2002/0103527 | A1 | 8/2002 | Kocur et al. |
| 2002/0138048 | A1 | 9/2002 | Tuch |
| 2003/0021825 | A1 | 1/2003 | Pathak et al. |
| 2003/0068353 | A1 | 4/2003 | Chen et al. |
| 2003/0125803 | A1 | 7/2003 | Vallana et al. |
| 2003/0208256 | A1 | 11/2003 | DiMatteo et al. |
| 2004/0006382 | A1 | 1/2004 | Sohier |
| 2004/0023339 | A1 | 2/2004 | Karpas |
| 2004/0024449 | A1 | 2/2004 | Boyle |
| 2004/0037889 | A1 | 2/2004 | Richeal et al. |
| 2004/0106984 | A1 | 6/2004 | Stinson |
| 2004/0133270 | A1 | 7/2004 | Grandt |
| 2004/0148012 | A9 | 7/2004 | Jang |
| 2005/0043783 | A1 | 2/2005 | Amis |
| 2005/0055080 | A1 | 3/2005 | Istephanous et al. |
| 2005/0060020 | A1 | 3/2005 | Jenson |
| 2005/0070996 | A1 | 3/2005 | Dinh et al. |
| 2005/0080481 | A1 | 4/2005 | Madda et al. |
| 2005/0145307 | A1 | 7/2005 | Shireman et al. |
| 2005/0177226 | A1 | 8/2005 | Banik et al. |
| 2005/0186241 | A1 | 8/2005 | Boyle et al. |
| 2005/0208100 | A1 | 9/2005 | Weber et al. |
| 2005/0272806 | A1 | 12/2005 | Falotico et al. |
| 2005/0278016 | A1 | 12/2005 | Welsh et al. |
| 2006/0004437 | A1 | 1/2006 | Jayaraman |
| 2006/0064157 | A1 | 3/2006 | Shanley |
| 2006/0093729 | A1 | 5/2006 | Marx et al. |
| 2006/0122689 | A1 | 6/2006 | Kocur et al. |
| 2006/0129231 | A1 | 6/2006 | De Scheerder et al. |
| 2006/0147489 | A1 | 7/2006 | Shanley et al. |
| 2006/0155369 | A1 | 7/2006 | Edwin et al. |
| 2006/0212109 | A1 | 9/2006 | Sirhan et al. |
| 2006/0224234 | A1 | 10/2006 | Jayaraman |
| 2006/0224237 | A1 | 10/2006 | Furst et al. |
| 2007/0005124 | A1 | 1/2007 | De Scheerder et al. |
| 2007/0027531 | A1 | 2/2007 | Dimatteo et al. |
| 2007/0043423 | A1 | 2/2007 | Grewe |
| 2007/0055352 | A1 | 3/2007 | Naimark et al. |
| 2007/0061007 | A1 | 3/2007 | Nolting |
| 2007/0112417 | A1 | 5/2007 | Shanley et al. |
| 2007/0123805 | A1 | 5/2007 | Shireman et al. |
| 2007/0168021 | A1 | 7/2007 | Holmes, Jr. et al. |
| 2007/0173923 | A1 | 7/2007 | Savage et al. |
| 2007/0219628 | A1 | 9/2007 | Shanley et al. |
| 2007/0282419 | A1 | 12/2007 | Hilaire et al. |
| 2008/0003251 | A1 | 1/2008 | Zhou |
| 2008/0051882 | A1 | 2/2008 | Rubin |
| 2008/0065201 | A1 | 3/2008 | Li |
| 2008/0077233 | A1 | 3/2008 | Diaz et al. |
| 2008/0183281 | A1 | 7/2008 | Rea et al. |
| 2008/0188925 | A1 | 8/2008 | Zhao |
| 2008/0195170 | A1 | 8/2008 | Asgari |
| 2008/0195196 | A1 * | 8/2008 | Asgari ............... 623/1.39 |
| 2008/0208313 | A1 | 8/2008 | Yu et al. |
| 2008/0234809 | A1 | 9/2008 | Greenan |
| 2008/0249599 | A1 | 10/2008 | Allen et al. |
| 2008/0255659 | A1 | 10/2008 | Huang et al. |
| 2008/0276935 | A1 | 11/2008 | Wang |
| 2008/0306579 | A1 | 12/2008 | Dolan et al. |
| 2009/0024209 | A1 | 1/2009 | Ozdil et al. |
| 2009/0024210 | A1 | 1/2009 | Klocke et al. |
| 2009/0035351 | A1 | 2/2009 | Berglund et al. |
| 2009/0061071 | A1 | 3/2009 | McMorrow et al. |
| 2009/0093871 | A1 | 4/2009 | Rea et al. |
| 2009/0105806 | A1 * | 4/2009 | Benjamin et al. ............... 623/1.15 |
| 2009/0132031 | A1 | 5/2009 | Cook et al. |
| 2009/0157172 | A1 | 6/2009 | Kokate et al. |
| 2009/0163995 | A1 | 6/2009 | Shanley et al. |
| 2009/0192593 | A1 | 7/2009 | Meyer et al. |
| 2009/0220612 | A1 | 9/2009 | Perera |
| 2009/0228095 | A1 | 9/2009 | Shanley et al. |
| 2009/0281615 | A1 | 11/2009 | Kocur et al. |
| 2009/0312833 | A1 | 12/2009 | Tittelbach et al. |
| 2009/0319026 | A1 | 12/2009 | Meyer |
| 2010/0010621 | A1 | 1/2010 | Klocke |
| 2010/0023115 | A1 | 1/2010 | Robaina et al. |
| 2010/0036482 | A1 | 2/2010 | Svrluga et al. |

(56) References Cited

U.S. PATENT DOCUMENTS

| | | |
|---|---|---|
| 2010/0057196 A1 | 3/2010 | Pathak |
| 2010/0070022 A1 | 3/2010 | Kuehling |
| 2010/0082096 A1 | 4/2010 | Gregorich |
| 2010/0145437 A1 | 6/2010 | Girton et al. |

FOREIGN PATENT DOCUMENTS

| | | |
|---|---|---|
| EP | 836839 B1 | 7/2006 |
| EP | 2191789 A1 * | 6/2010 |
| WO | WO94/18956 | 9/1994 |
| WO | WO96/19255 | 6/1996 |
| WO | WO96/26682 | 9/1996 |
| WO | WO98/23228 | 6/1998 |
| WO | WO00/01322 | 1/2000 |
| WO | WO02/060506 | 8/2002 |
| WO | WO03/092547 | 11/2003 |
| WO | WO2007/021749 | 2/2007 |

OTHER PUBLICATIONS

U.S. Appl. No. 07/644,802, filed Jan. 22, 1991, Hodgson, et al.
U.S. Appl. No. 09/716,146, filed Nov. 17, 2000, Boyle.
U.S. Appl. No. 11/868,742, filed Oct. 8, 2007, Rea.
U.S. Appl. No. 11/941,591, filed Nov. 16, 2007, Cook et al.
U.S. Appl. No. 12/428,581, filed Apr. 23, 2009, Hoff et al.
U.S. Appl. No. 12/500,359, filed Jul. 9, 2009, Storment et al.
U.S. Appl. No. 12/767,099, filed Apr. 26, 2010, Melder.
U.S. Appl. No. 12/834,274, filed Jul. 12, 2010, Storment et al.
U.S. Appl. No. 12/884,287, filed Sep. 17, 2010, Bienvenu.
U.S. Appl. No. 12/884,343, filed Sep. 17, 2010, Bienvenu.
U.S. Appl. No. 12/884,362, filed Sep. 14, 2010, Mitchell et al.
U.S. Appl. No. 12/884,451, filed Sep. 17, 2010, Mitchell et al.
U.S. Appl. No. 12/884,501, filed Sep. 17, 2010, Melder.
U.S. Appl. No. 12/884,503, filed Sep. 17, 2010, Mitchell et al.
U.S. Appl. No. 12/884,551, filed Sep. 17, 2010, Mauch.
U.S. Appl. No. 12/884,578, filed Sep. 17, 2010, Avelar et al.
Polacco et al. "Biodegradable Hollow Fibres Containing Drug-Loaded Nanoparticles as Controlled Release Systems" Polym International 51:1464-1472 (2002).
PCT Search Report PCT/US2010/039087.
PCT Search Report PCT/US2010/049439.
PCT Search Report PCT/US2010/049437.
PCT Search Report PCT/US2010/049434.
Basarir et al., "Osseointegration in Arthroplasty: Can Simvastatin Promote one response to Implants?" International Orthopedics (SICOT) (2009) 33:855-859.
Derle et al., "Particle Engineering Techniques to Enhance Dissolution of Poorly Water Soluble Drugs" International Journal of Current Pharmaceutical Research, vol. 2, Issue 1, 2010, pp. 10-15.
Purvis et al., "Cryogenic Liquids, Nanoparticles, and Microencapsulation" International Journal of Pharmaceutics, 2006.
"Breakthrough Solubilization Technology Targets Stubborn Drug Candidates" Dowpharma.
"Supercritical Carbon-Dioxide Cleaning Defined" Supercritical Carbon-Dioxide Cleaning Technology Review, Jul. 1996.
Berger "Coating Drug-Eluting Arterial Stents Using Ultrasonic Spray Nozzle" !ILASS Americas, 19$^{th}$ Annual Conference on Liquid Atomization and Spray Systems, May 2006.

* cited by examiner

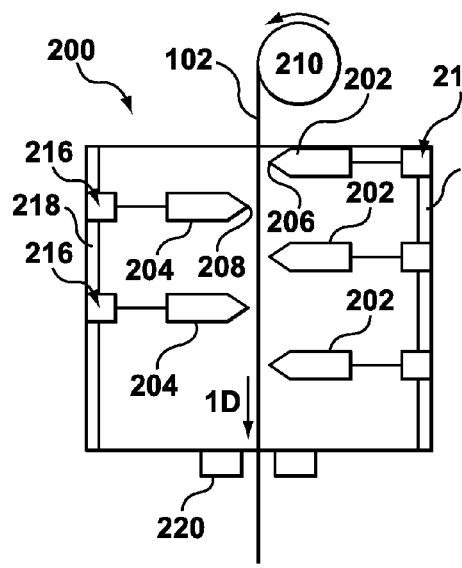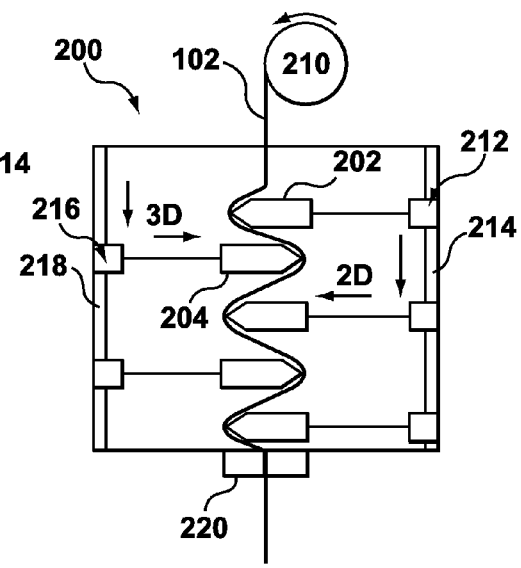
FIG. 8  FIG. 9
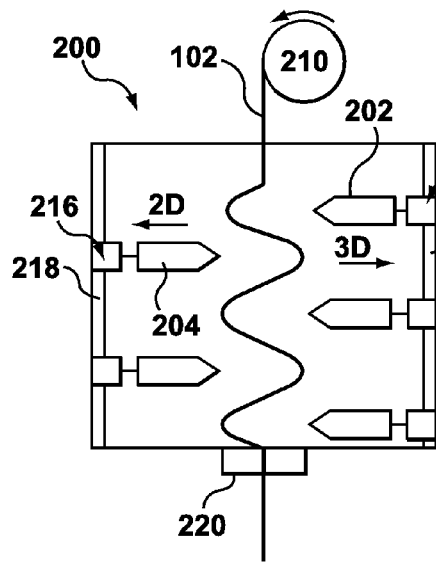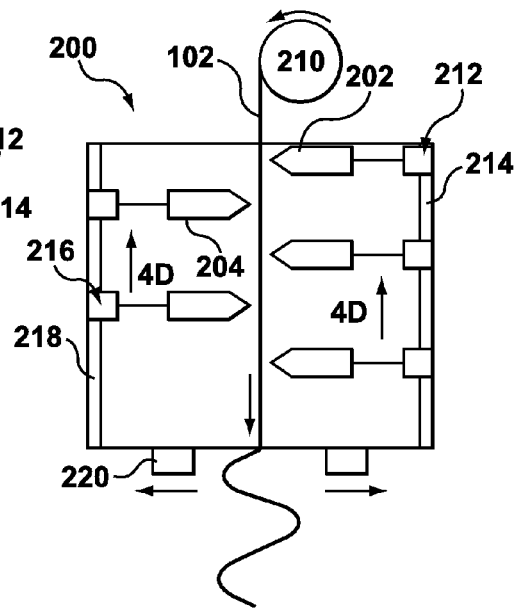
FIG. 10  FIG. 11

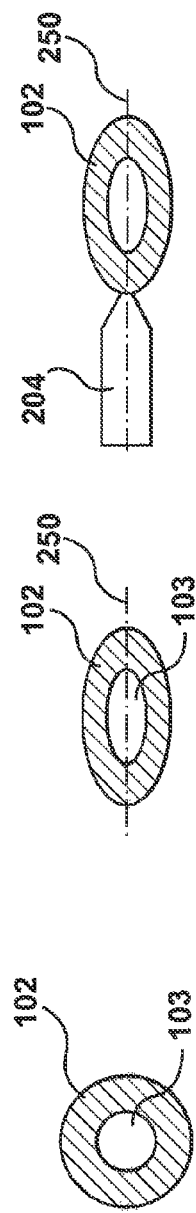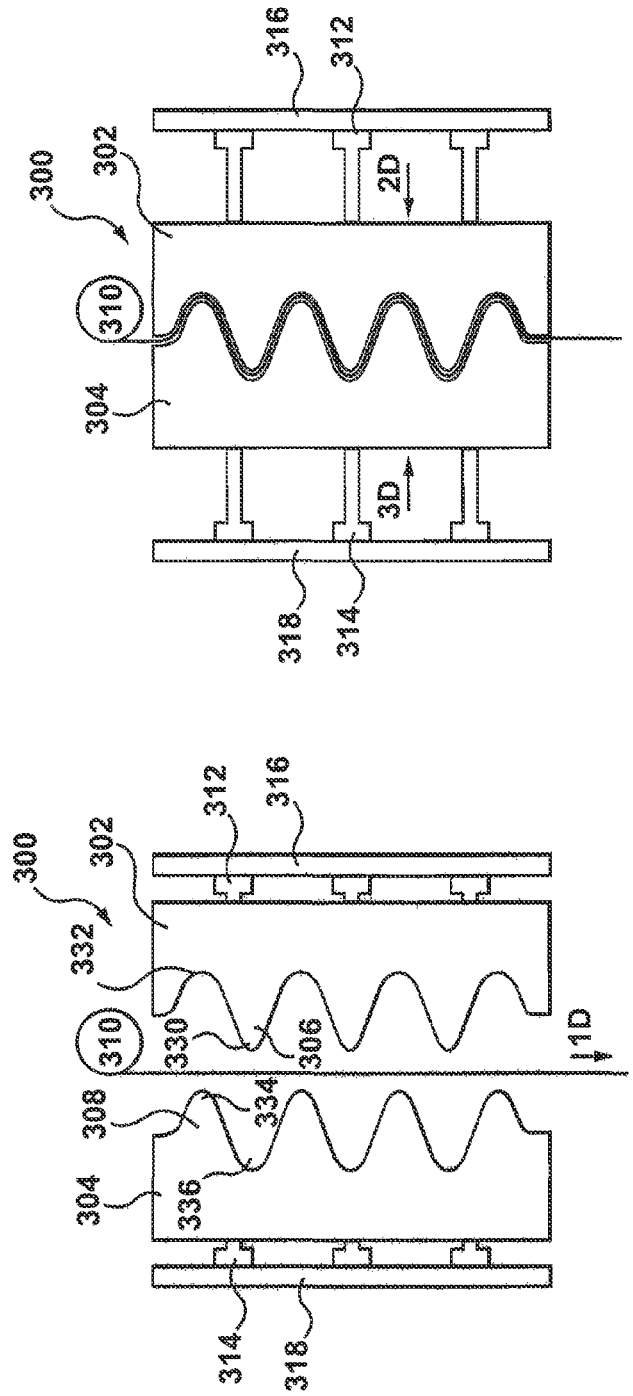

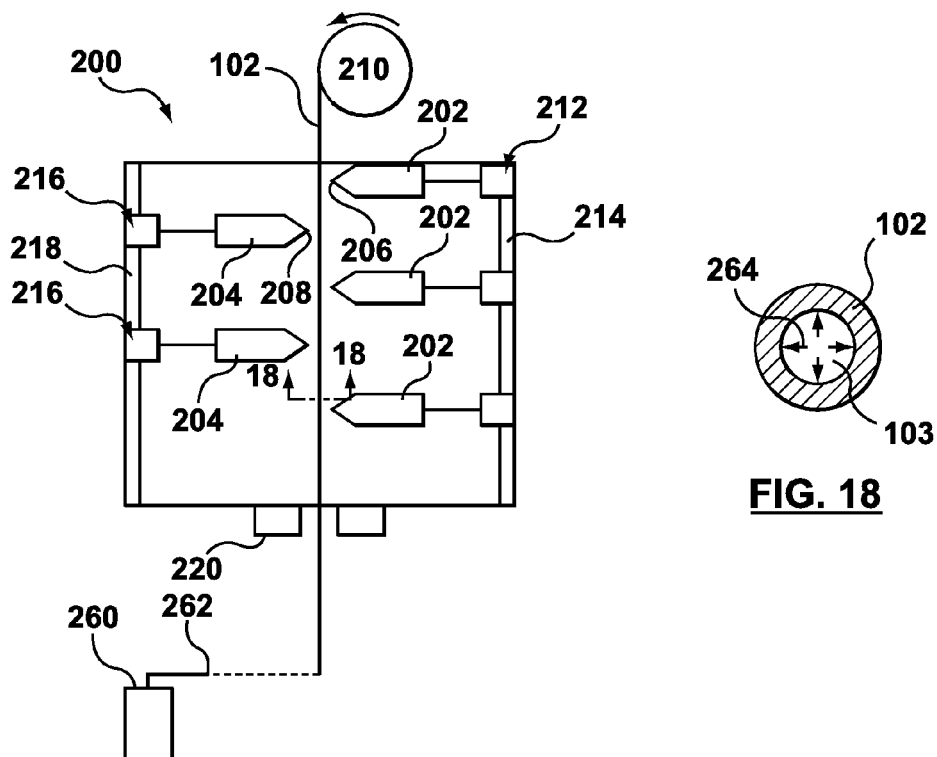
FIG. 17
FIG. 18
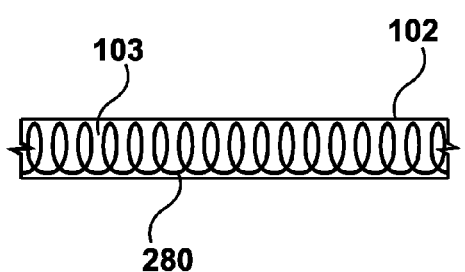
FIG. 19
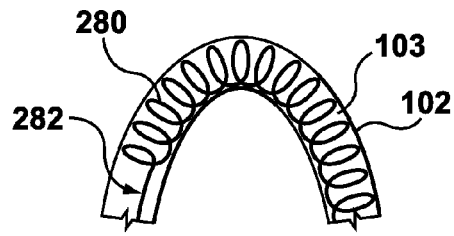
FIG. 20
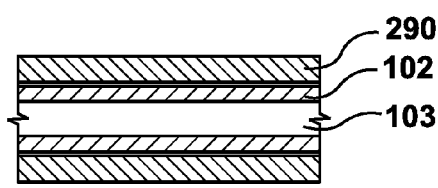
FIG. 21
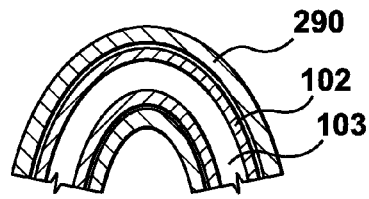
FIG. 22

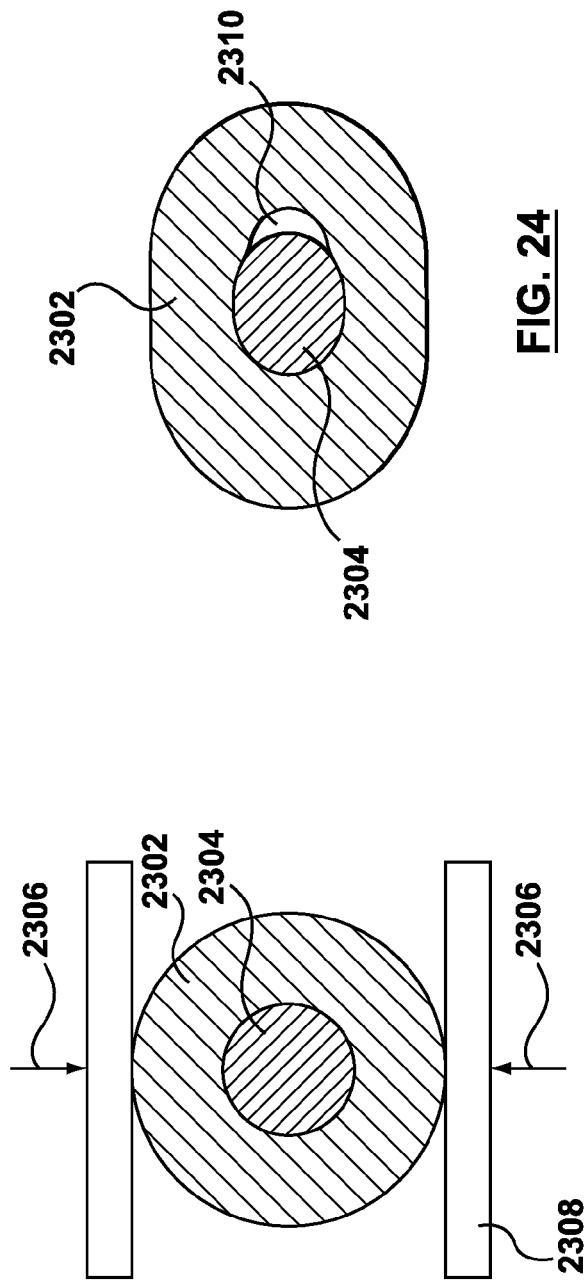
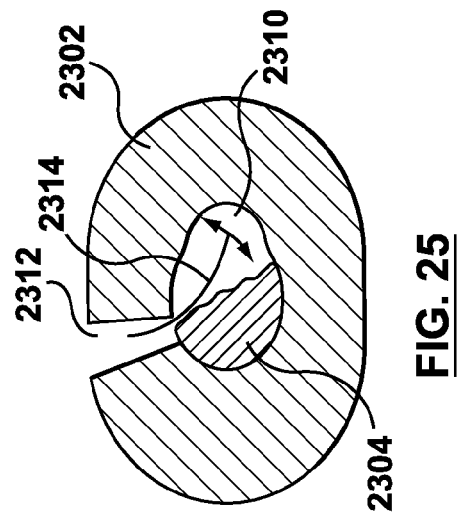

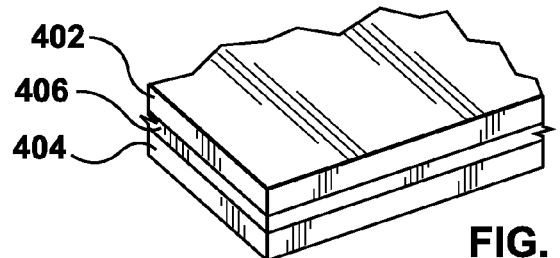
FIG. 26
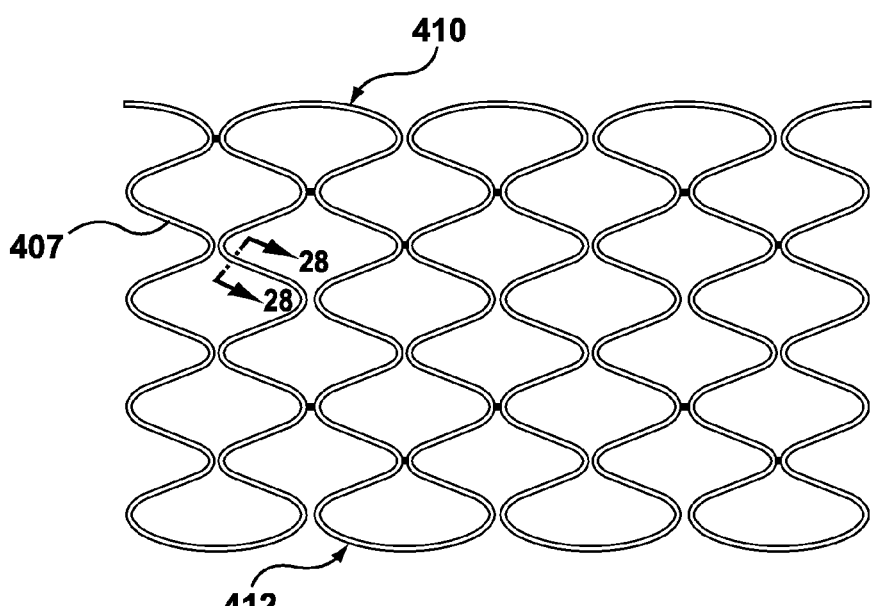
FIG. 27
FIG. 28
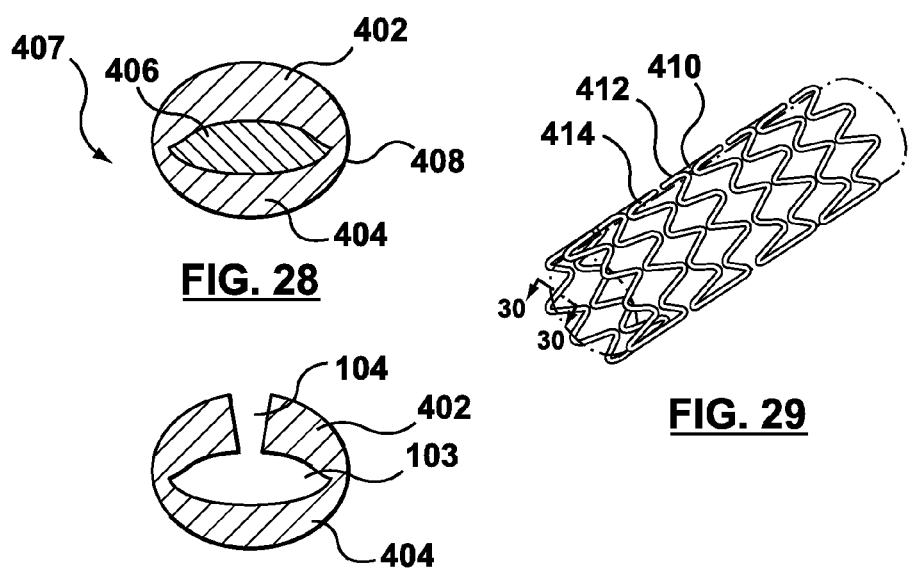
FIG. 29
FIG. 30

METHOD OF FORMING HOLLOW TUBULAR DRUG ELUTING MEDICAL DEVICES

CROSS-REFERENCE TO RELATED APPLICATION

This application is a Continuation of and claims the benefit of U.S. patent application Ser. No. 12/884,551 filed Sep. 17, 2010; which claims the benefit of U.S. Provisional Patent Application No. 61/244,049 filed Sep. 20, 2009, the contents of which is hereby incorporated by reference.

FIELD OF THE INVENTION

The present invention relates to implantable medical devices that release a therapeutic substance and methods of forming such medical devices.

BACKGROUND OF THE INVENTION

Drug-eluting implantable medical devices have become popular in recent times for their ability to perform their primary function (such as structural support) and their ability to medically treat the area in which they are implanted.

For example, drug-eluting stents have been used to prevent restenosis in coronary arteries. Drug-eluting stents may administer biologically or pharmacologically active substances such as anti-inflammatory compounds that block local invasion/activation of monocytes, thus preventing the secretion of growth factors that may trigger VSMC proliferation and migration. Other potentially anti-restenotic compounds include anti-proliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a biologically or pharmacologically active substance or a combination of biologically or pharmacologically active substances. Once the medical device is implanted at a target location, the biologically or pharmacologically active substance is released from the polymer for treatment of the local tissues. The biologically or pharmacologically active substance is released by a process of diffusion through the polymer layer for biostable polymers, and/or as the polymer material degrades for biodegradable polymers.

Controlling the rate of elution of a biologically or pharmacologically active substance from the drug impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the biologically or pharmacologically active substance from reaching the target site. Still further, drug impregnated polymer coatings are limited in the quantity of the biologically or pharmacologically active substance to be delivered by the amount of a biologically or pharmacologically active substance that the polymer coating can carry and the size of the medical devices. Controlling the rate of elution using polymer coatings is also difficult.

Accordingly, drug-eluting medical devices that enable increased quantities of a biologically or pharmacologically active substance to be delivered by the medical device, and allow for improved control of the elution rate of the biologically or pharmacologically active substance, and improved methods of forming such medical devices are needed.

SUMMARY OF INVENTION

In an embodiment of a method of forming a stent, the lumen of a hollow wire is filled with a fluid to form a supported hollow wire. The supported hollow wire is shaped into a stent pattern. Openings are formed through the wire to access the lumen. The supported hollow wire is processed to remove the fluid from the lumen of the outer member without adversely affecting the outer member, leaving the hollow wire shaped into a stent pattern. The lumen is filled with a biologically or pharmacologically active substance. The fluid may be pressurized prior to shaping the support hollow wire into the stent pattern.

In another embodiment of a method of forming a stent, the lumen of a hollow wire is filled with a liquefied wax. The liquefied wax is allowed to solidify or harden within the lumen to form a supported hollow wire. The supported hollow wire is shaped into a stent pattern. Openings are formed through the wire to access the lumen. The supported hollow wire is processed to remove the wax from the lumen without adversely affecting the wire, leaving the hollow wire shaped into a stent pattern. The lumen may then be filled with a biologically or pharmacologically active substance.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 8-11 are schematic illustrations of a method of forming wave forms in a wire.

FIG. 12-14 are cross-sectional views of hollow wire in a method of forming a hollow wire into a stent in accordance with an embodiment hereof.

FIGS. 15-16 are schematic illustrations of a method of forming a wave form in a hollow wire in accordance with an embodiment hereof.

FIG. 17 is a schematic illustration of an apparatus for forming a wave form in a hollow wire in accordance with an embodiment hereof.

FIG. 18 is a cross-section view of a hollow wire taken along line 18-18 of FIG. 17.

FIGS. 19-20 are schematic illustrations of a hollow wire including a spring element in the lumen of the hollow wire.

FIGS. 21-22 are cross-sectional views of a portion of a hollow wire including a supporting element surrounding the hollow wire.

FIGS. 23-25 are cross-sectional views of a hollow wire with an outer member and an inner member, wherein the outer member is deformed to form a lumen between the outer and inner members.

FIGS. 26-30 are schematic illustrations of a method for forming a stent with hollow struts in accordance with an embodiment hereof.

DETAILED DESCRIPTION OF THE INVENTION

Specific embodiments of the present invention are now described with reference to the figures, where like reference numbers indicate identical or functionally similar elements.

Figure 1:
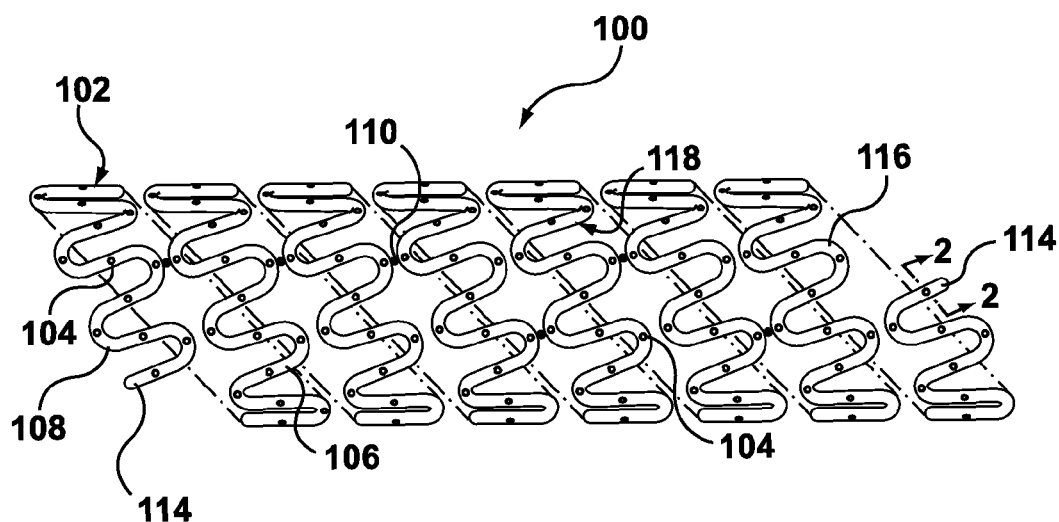
FIG. 1 is a schematic illustration of an exemplary stent in accordance with an embodiment hereof.
Figures 2, 3:
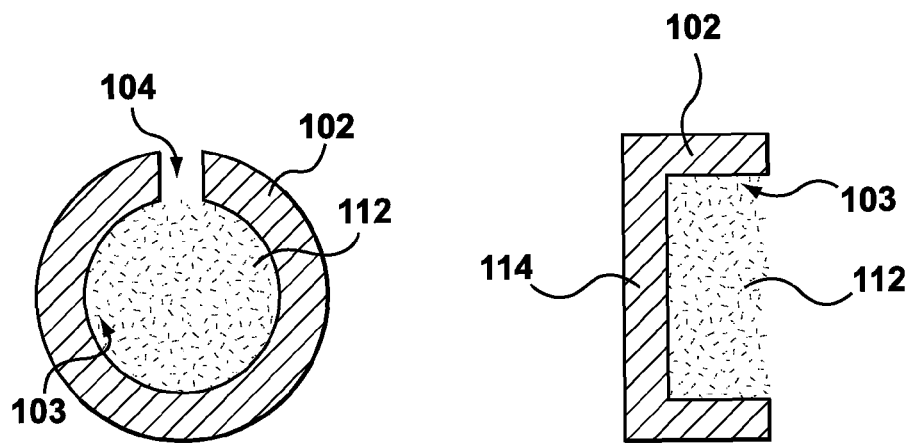
FIG. 2 is a cross-sectional view taken along line 2-2 of FIG. 1.
FIG. 3 is a longitudinal cross-section of an end of the wire of the stent of FIG. 1.
Figure 4:
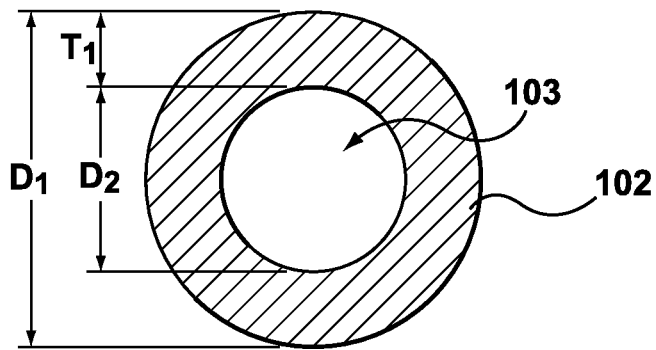
FIGS. 4-7 are cross-sectional views of a hollow wire in accordance with an embodiment hereof.
Figure 5:
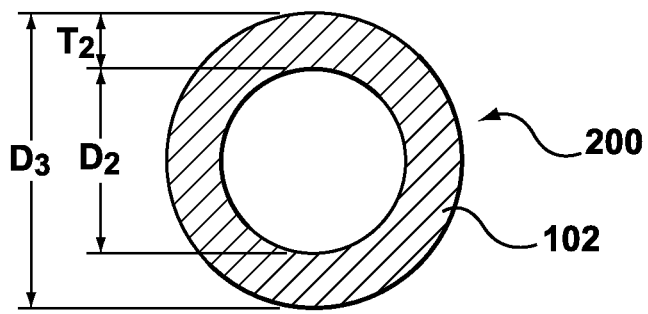

An embodiment of a stent 100 disclosed herein is shown in FIGS. 1-3. In particular, stent 100 is formed from a hollow wire 102. In the embodiment shown in FIG. 1, stent 100 is formed into a series of generally sinusoidal waves including generally straight segments or struts 106 joined by bent segments or crowns 108 and form a generally tubular stent 100. The generally sinusoidal pattern is formed into a tube, as shown in FIG. 1. In the embodiment shown in FIG. 1, selected crowns 108 of longitudinally adjacent sinusoids may be joined by, for example, fusion points 110. The invention hereof is not limited to the pattern shown in FIG. 1. Stent 100 can be formed into any pattern suitable for use as a stent. For example, and not by way of limitation, stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As shown in FIG. 2, hollow wire 102 of stent 100 allows for a biologically or pharmacologically active substance 112 to be deposited within the lumen 103 of hollow wire 102. Although hollow wire 102 is shown as generally having a circular cross-section, hollow wire 102 may be generally elliptical or rectangular in cross-section. Hollow wire 102 further includes cuts or openings 104 dispersed along its length to permit biologically or pharmacologically active substance 112 to be released from lumen 103. Openings 104 may be disposed only on generally straight segments 106 of stent 100, only on crowns 108 of stent 100, or both generally straight segments 106 and crowns 108. Openings 104 may be sized and shaped as desired to control the elution rate of biologically or pharmacologically active substance 112 from stent 100. Larger sized openings 104 generally permit a faster elution rate and smaller sized openings 104 generally provide a slower elution rate. Further, the size and/or quantity of openings 104 may be varied along stent 100 in order to vary the quantity and/or rate of biologically or pharmacologically active substance 112 being eluted from stent 100 at different portions of stent 100. Openings 104 may be, for example and not by way of limitation, 5-30 µm in diameter. Openings 104 may be provided only on an outwardly facing or abluminal surface 116 of stent 100, as shown in FIG. 2, only on the inwardly facing or luminal surface 118 of stent 100, both surfaces, or may be provided anywhere along the circumference of wire 102. Openings 104 may have a constant diameter through the depth or have a tapered or conical shape.

Ends 114 of wire 102 may be closed, as shown in FIG. 3. Ends 114 may be closed by crimping excess material of wire 102 to close lumen 103. Closing ends 114 prevents drug 114 from prematurely releasing from ends 114. However, closing ends 114 is not required as drug 112 may be dried, provided within a polymer matrix, enclosed within a liner (not shown), or otherwise protected from premature release from ends 114. Further, ends 114 may be welded, crimped or otherwise connected to other portions of wire 102 such that the ends 114 are not free ends. Ends 114 may alternatively be provided as free ends.

Embodiments for Bending a Hollow Wire

Forming a hollow wire stent by bending a hollow wire into a stent form may cause kinking, cracking, or other undesirable properties in the finished stent. Accordingly, co-pending U.S. application Ser. No. 12/500,359, filed Jul. 9, 2009, incorporated by reference herein in its entirety, describes methods for forming a hollow wire stent by forming a core wire, bending the core wire into the selected stent shape, and then removing the sacrificial or inner member of the core wire. However, it may be beneficial to form the stent using a hollow wire if concerns regarding kinking or cracking can be overcome.

Figure 31:
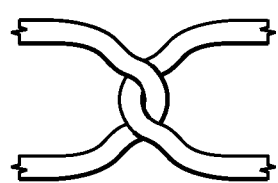
FIGS. 31-36 are schematic illustrations of method of bonding adjacent crowns of a stent.
Figure 32:
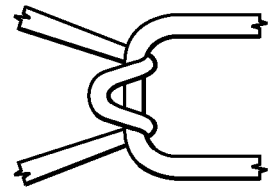
Figure 33:
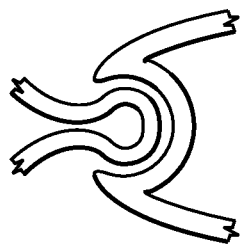
Figure 34:
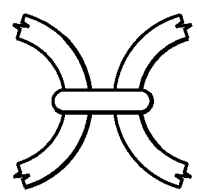
Figure 35:
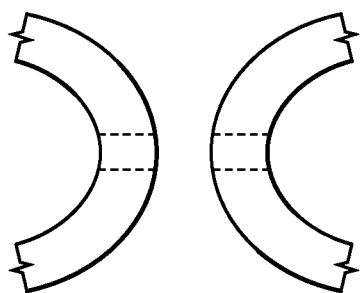
Figure 36:
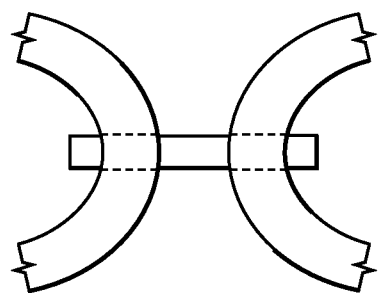

A method for forming a stent pattern from a wire utilizes fingers to bend the wire into the desired pattern. An example of such a system is described in co-pending U.S. patent application Ser. No. 12/428,581, filed Apr. 23, 2009, which is incorporated by reference herein in its entirety. Other systems may also be used to bend the wire into the desired pattern. The pattern, such as a sinusoidal pattern, is then wrapped around a mandrel and selected crowns may be bonded together to form a stent. The crowns may be bonded together by welding, or other methods of bonding such as mechanical means, spring clips, interconnecting crowns, adhesives, brazing, solder, rivets, sutures, or other suitable means known to those skilled in the art. FIGS. 31-36 show examples of such alternative bonding methods. FIGS. 31 and 32 show interconnecting crowns. The crowns can be electropolished, swaged, or otherwise processed after interconnection in order to reduce the profile of the interconnection. FIG. 33 also shows interconnecting crowns in ball and socket type of interconnection. The crowns can be swaged to lock the "ball" into the "socket". FIG. 34 shows the crowns coupled to each other with a suture. The suture can be made of any material suitable to couple the crowns together. FIGS. 35-36 show a rivet connection, wherein the holes are drilled through the crowns as shown in FIG. 35 and a rivet is inserted through the holes to connect the crowns, as shown in FIG. 36. It is understood that these are merely examples of connections between the crowns, and that those skilled in the art would recognize other alternative connections.

FIGS. 4-7 show cross-sectional views of hollow wire 102 in a method of forming a stent from a hollow wire. Wires forming stents are generally as thin as possible while still providing radial strength in the stent form. In a hollow wire coronary stent, an example of an inner diameter for the wire is about 0.0015 inch and an outer diameter is of about 0.0035 inch. The dimension range for the wire in a coronary hollow wire stent is an outside diameter range of 0.002 inches to 0.005 inches with an inside diameter of 50% or less of the outside diameter. The dimension range for the wire in a peripheral or other anatomy location hollow wire stent/implant is an outside diameter range of 0.002 inches to 0.012 inches with an inside diameter of 75% or less of the outside diameter. In the embodiment shown in FIGS. 4-7, a hollow wire 102 is shaped into a stent pattern. In this embodiment, a relatively large outer diameter $D_1$ compared to the inner diameter $D_2$ is utilized, resulted in a relatively thick wall of hollow wire 102. Due to the relatively large outer diameter $D_1$ relative to the inner diameter $D_2$, (i.e., thick wall) kinking, cracking, or closing of the lumen 103 is reduced or prevented. The stent pattern can be the pattern shown in FIG. 1 or any other suitable pattern formed from a wire. Shaping wire 102 into the stent pattern shown in FIG. 1 generally includes the steps of forming wire 102 into a two dimensional sinusoid pattern followed by wrapping the pattern around a mandrel, as known to those skilled in the art. The end result is a helical stent pattern formed onto a mandrel.

Figure 6:
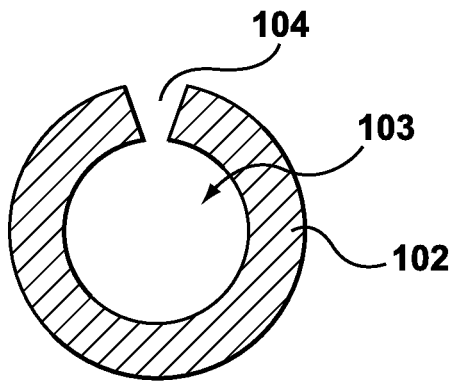

After wire 102 has been shaped into the stent pattern, wire 102 is electropolished or otherwise processed to remove material from wire 102. Additional removal processes include but are not limited to plasma etching, sand blasting, bead blasting, acid etching, tumbling, grinding and laser etching. The acid etching processes may include any wet chemical etching mixture that attacks the metals directly. Examples are heated mixtures of, $HF:HNO_3$ (hydrofluoric & nitric acids) or $HCl:H_2O_2$ (hydrochloric & hydrogen peroxide), both mixtures can etch the metals directly. Many other wet metal etch mixtures exist. Such processing reduces the outer diameter of wire 102. Accordingly, as shown in FIG. 6, outer diameter $D_3$ of wire 102 may be about 0.0035 inch while inner diameter $D_2$ remains about 0.0015 inch, with a wall thickness $T_2$ of about 0.001 inches. The material removal process will alter the dimension, but the proportion of outside diameter to inside diameter dimension would stay within the limits of inside diameter being 50% or less of the outside diameter for coronary applications and the inside diameter being 75% or less of the outside diameter for applications outside of the coronary vasculature. After removing the appropriate amount of material, selected crowns 108 of the helical pattern may be bonded together or alternatively the material can be removed after the bonding process.

Figure 7:
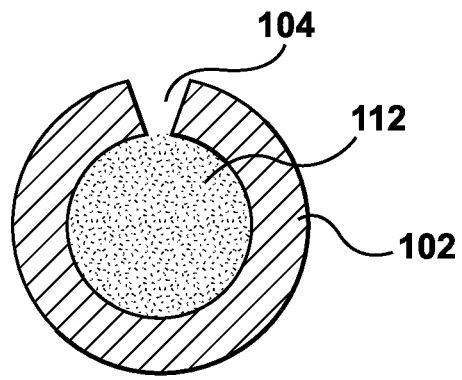

Openings 104 may then be provided through wire 102. Openings 104 may be laser cut, drilled, etched, or otherwise provided in wire 102, as shown in FIG. 6. A biologically or pharmacologically active substance 112 may be injected into lumen 103 of outer member 102 as shown FIG. 7. This produces a hollow wire 102 with biologically or pharmacologically active substance 112 disposed in lumen 103 thereof, and openings 104 through which biologically or pharmacologically active substance 112 may be eluted, as shown in FIG. 7.

In another embodiment of a method for forming a hollow wire stent, a hollow metal wire is provided. The wire is heated to a temperature to soften the material. The wire is then shaped into a stent pattern, as described above. By heating the hollow wire prior to shaping the hollow wire into the stent pattern, kinking, cracking, and other deformations may be reduced or eliminated. In a particular, non-limiting example, a hollow wire made from MP35N is heated to 1140 Kelvin to 1450 Kelvin and formed into a stent shape at this elevated temperature. Openings are then formed through the hollow wire to the lumen and the stent is filled with a drug, as described above. Other materials such as but not limited to 316 stainless steel, tantalum, niobium, molybdenum-rhenium alloys, nickel-titanium alloys, L605, magnesium and magnesium alloys may be used to form the hollow wire, and may be heated to 65% to 85% of the absolute melting temperature to soften the material prior to forming Another method for forming a stent from a hollow wire is shown in FIGS. 8-11. As discussed above, a method process for forming a wire into a stent form utilizes fingers to bend a straight wire. Schematically represented in FIGS. 8-11, and described in more detail in U.S. application Ser. No. 12/428, 581, filed Apr. 23, 2009, which is incorporated herein in its entirety, is a portion of an apparatus 200 for forming a wave form for a stent from a hollow wire 102. Briefly describing apparatus 200, the hollow wire 102 is provided to the apparatus 200 by a supply 210, which may include a spool upon which the hollow wire 102 is wound. Alternatively the hollow wire can be provided to the apparatus in discrete sections. The hollow wire 102 may be fed in the first direction 1D along an axis into a wire forming area. A suitable clamp 220 may be located just outside the wire forming area, as illustrated, or may be located within the wire forming area. The clamp 220 is configured to clamp the hollow wire 102 so that tension may be applied to the hollow wire 102 as the hollow wire 102 is formed into a predetermined shape. The apparatus 200 also includes a plurality of first forming members or fingers 202 located on one side of the hollow wire 102 and a plurality of second forming members or fingers 204 located on the opposite side of the hollow wire 102. The first and second forming members 202, 204 have substantially elongated shapes and include wire engaging surfaces 206, 208, respectively.

As shown in FIG. 9, first forming members 202 move in a second direction 2D that is substantially orthogonal to the first direction 1D to engage hollow wire 102. After the wire engaging surfaces 206 have engaged the hollow wire 102, the first forming members 202 continue to move in the second direction 2D to deform the hollow wire 102, as shown in FIG. 9. Each of the first forming members 202 may be moved in the second direction 2D by a respective first actuator 212, all of which may be configured to move in the first direction 1D along a suitable structure, such as a rail 214. Similarly, second forming members 204 move in a third direction 3D such that wire engaging surfaces 208 engage hollow wire 102. After the wire engaging surfaces 206 have engaged the hollow wire 102, the second forming members 204 continue to move in the third direction 3D to deform the hollow wire 102, as shown in FIG. 9.

As illustrated in FIG. 10, after a wave form has been formed, the first forming members 202 may be moved in the third direction 3D to disengage from the wire hollow 102, and the second forming members 204 may be moved in the second direction 2D to disengage from the hollow wire 102. The clamp 220 may then be opened and wire 102 may be advances by supply 210 so that a new section of hollow wire 102 may be advanced into the wire forming area, as shown in FIG. 11. At about the same time, the first and second forming members 202, 204 may be moved along their respective rails 212, 214 in the fourth direction 4D so that another cycle may begin. It would be understood by those skilled in the art that this description is merely an example of method to bend a wire into a wave form for a stent.

In order to reduce or eliminate the kinking, cracking, closing of lumen 103, or other deformations, hollow wire 102 may be swaged or otherwise processed to alter its cross-sectional shape to be generally elliptical. Thus, a hollow wire 102 of generally circular cross-section, as shown in FIG. 12, is swaged or otherwise processed to form a wire 102 with a generally elliptical cross-section, as shown in FIG. 13. Swaging or other processes to alter the cross-sectional shape could be done only at select locations such as crowns. The generally elliptically shaped wire includes a long axis 250 in cross-section, as shown in FIG. 13. The forming members 204, 206 (only one is shown in FIG. 14) are aligned with the long axis 250 of the hollow wire 102, as shown in FIG. 14. The process as described with respect to FIGS. 8-11 is then performed to bend hollow wire 102 into the wave form for a stent and wrapped around a mandrel to form the stent pattern. Selected crowns of the stent pattern may then be bonded together, openings 104 may be cut through the wall of hollow wire 102 to access lumen 103, and the lumen filled with a biologically or pharmacologically active substance, as described above. Alternatively, the swaging or other processes to alter the cross-sectional shape could be done after forming to return the cross section to a circular or more circular shape if the wires become elliptical during forming. The forming could be done only at select locations such as crowns.

Figure 38:
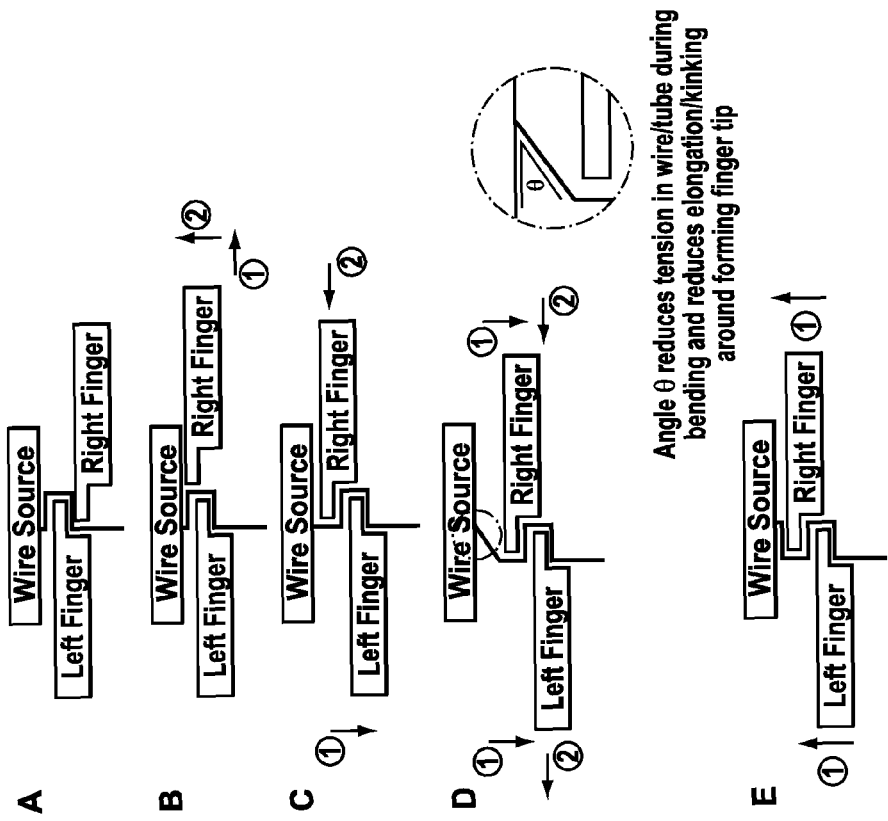
FIGS. 37-38 are schematic illustrations of an apparatus and methods of forming a wave form in a wire.
Figure 37:
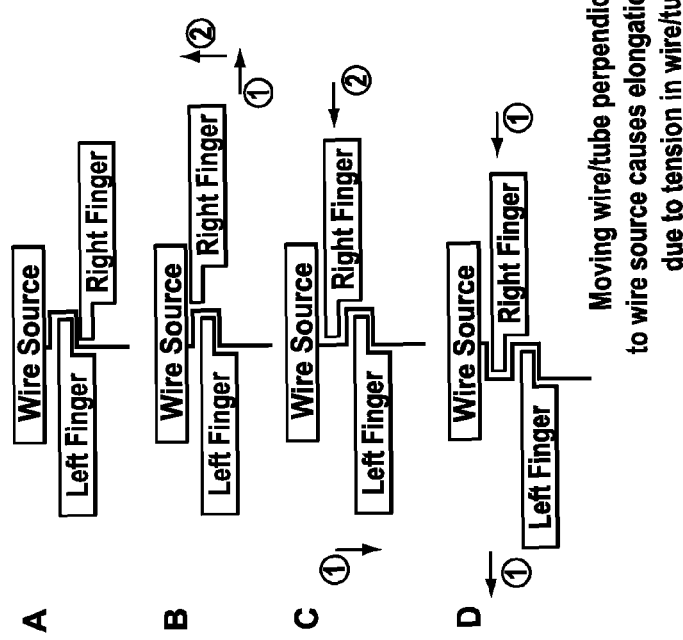

Using the method described generally at FIGS. 8-11, hollow wire 102 is bent into shape at a speed of 20-100 mm/s for the forming members with a preferable speed of approximately 60 mm/s. In another method of reducing kinking, cracking, closing of the lumen, and other deformations, the rate of bending is reduced to the speed to 0.5-19 mm/s for the forming members. The radii of the forming members contacting the hollow wire should be 1-2.5 times the radius of the wire. An alternative forming movement to reduce tension and thereby reduce elongation of the hollow wire during bending is described in FIGS. 37 and 38. FIG. 37 shows steps A-D for forming a waveform in a wire in a similar fashion as described, for example, in U.S. application Ser. No. 12/428,581, filed Apr. 23, 2009, which is incorporated herein in its entirety. FIG. 38 shows steps A-E of an embodiment of a method for forming a waveform in a hollow wire, wherein a less severe angle θ is created in the wire, thereby reducing tension and elongation of the hollow wire.

Figure 39:
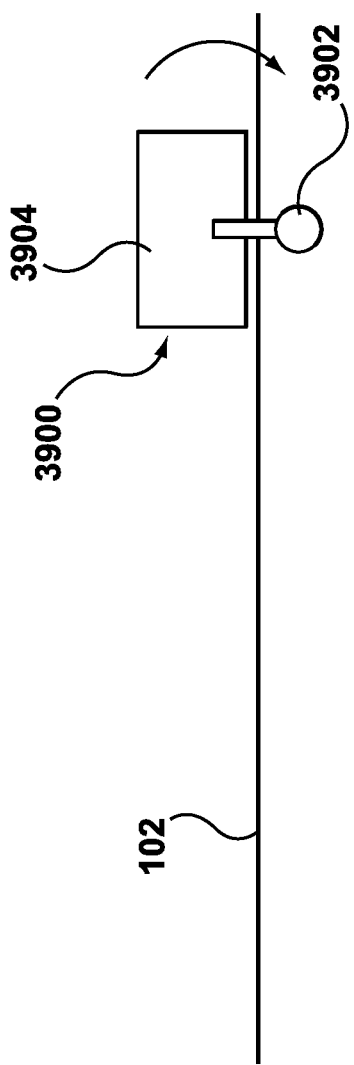
FIGS. 39-40 are schematic illustrations of an apparatus and method of forming a bend in a wire.
Figure 40:
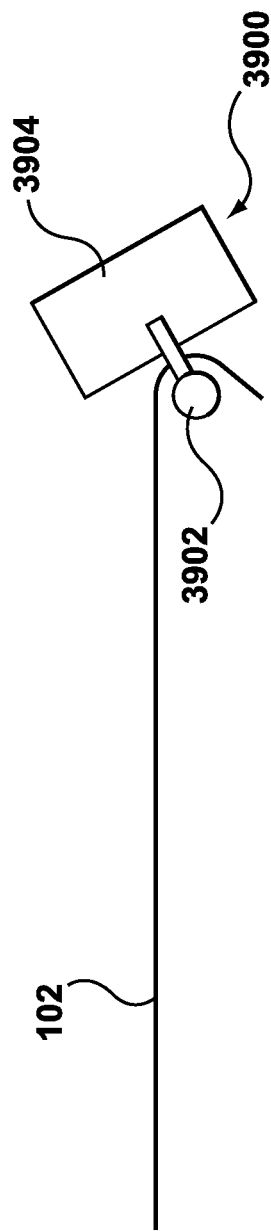

In another method, the hollow wire 102 is bent incrementally in order to reduce the risk of kinking, cracking, or other deformations. In particular, a hollow wire 102 is partially bent. Hollow wire 102 is then annealed to allow stress relief using a temperature of 50% of the absolute melt temperature of the material or greater. The hollow wire 102 is then further bent. The bending and annealing process may be repeated as necessary to bend hollow wire 102 while limiting kinking, cracking, or other deformation of the lumen 103. An embodiment of an apparatus 3900 for incrementally bending the hollow wire 102 is shown in FIGS. 39-40, although other apparatuses or methods for incrementally bending wire 102 may be used. Bending apparatus 3900 includes a roller element 3902 and a support element 3904. Rotating bending apparatus 3900 as indicated by the arrow bends wire 102.

In another embodiment, hollow wire 102 is bent into the desired waveform using a clamshell type apparatus 300. As shown in FIGS. 15 and 16, hollow wire 102 is provided to the apparatus 300 by a supply 310, which may include a spool upon which the hollow wire 102 is wound. Alternatively the hollow wire can be provided to the apparatus in discrete sections. The hollow wire 102 may be fed in the first direction 1D along an axis. A suitable clamp (not shown) may be provided to clamp the wire 102 so that tension may be applied to the wire 102 as hollow wire 102 is formed into a predetermined shape, as described above with respect to apparatus 300. The apparatus 300 also includes a first clamshell half 302 located on one side of hollow wire 102 and a second clamshell half 304 located on the opposite side of hollow wire 102. An end of first clamshell half 302 facing hollow wire 102 is shaped as a waveform 306 with a plurality of peaks 330 and valleys 332. An end of second clamshell half 304 facing hollow wire 102 is shaped as a waveform including a plurality of peaks 334 and valleys 336. Peaks 330 of first clamshell half 302 align with valleys 336 of second clamshell half 304 and peaks 334 of second clamshell half 304 align with valleys 332 of first clamshell half 302. The ends of clamshell halves 302, 304 opposite the waveforms 306, 308 are coupled to actuators 312, 314, respectively. Actuators 312, 314 may be coupled to rails 316, 318, respectively, or other suitable support structures.

Actuators 312 move first clamshell half 302 in direction 2D and actuators 314 move second clamshell half 304 in direction 3D, as shown in FIG. 16. Hollow wire 102 is deformed between peaks 330, 334 and valleys 336, 332, respectively such that hollow wire 102 becomes a waveform. Actuators 312, 314 then move first and second clamshell halves 302, 304 back to the position of FIG. 15, supply 310 feeds hollow wire 102 in direction 1D, and the process is repeated for another section of wire 102. By using clamshell halves 302, 304, hollow wire 102 is supported while being bent into the waveform to reduce kinking, cracking, and other deformations. Other forming options include using pair(s) of matching gears wherein the hollow wire sample is formed by the interlocking of the gear teeth.

Embodiments Bending a Supported Wire

As disclosed in co-pending U.S. application Ser. No. 12/500,359, filed Jul. 9, 2009, which is incorporated herein in its entirety, a method for reducing or preventing kinking, cracking, and other deformations in a hollow wire when shaping the hollow wire into a stent pattern is to internally support the wire during the shaping step, and then removing the supporting element after the wire has been shaped into the stent pattern. In some applications where the lumen is small, it may be difficult to remove the supporting element.

FIGS. 17 and 18 show an embodiment wherein the lumen 103 of a hollow wire 102 is coupled to a pump 260. Tubing 262 may be used to couple the pump 260 to the hollow wire 102. An end of lumen 103 may be plugged or otherwise closed to assist in building pressure in the lumen. Pump 260 pressurizes lumen 103 with a fluid, such as air, water, alcohol, oils (hydrocarbon or silicone based), waxes, meltable polymers, slurries of water and/or organic solvents and particles where the particles can be metal, silica or polymeric or other suitable fluids. As shown by the arrows 264 in FIG. 18, this fluid pressure supports the walls of hollow wire 102 while hollow wire 102 is shaped into a stent pattern using the apparatus 200 as described with respect to FIGS. 8-11, the method and apparatus described in co-pending U.S. application Ser. No. 12/428,581, filed Apr. 23, 2009, or suitable shaping apparatuses and methods. In certain embodiments, pump 260 may not be required. For example, when using relatively non-compressible fluids such as oils, water, and other non-compressible fluids known to those of ordinary skill in the art, the non-compressible fluid itself may sufficiently support hollow wire 102 during the process of shaping hollow wire 102 into a stent pattern.

Once hollow wire 102 has been shaped into the stent pattern, pump 260 is turned off (if used) and the fluid is drained from hollow wire 102. The fluid may be drained/removed by vacuum or pressure applied to the lumen, flushing the fluid out with another fluid, or other methods known to those skilled in the art. Further, any residual fluid remaining fluid may be vaporized during an annealing process step typically performed on stents.

In a non-limiting embodiment, a wax, such as an industrial grade wax such as paraffin, is liquefied/melted and inserted into the lumen 103 of hollow wire 102. Pressure or vacuum may be used to assist the liquefied wax fill lumen 103. The wax is permitted to solidify or harden within lumen 103, such as by cooling. The wire 102 is then shaped into the stent pattern with the wax supporting the walls of wire 102. After the wire has been shaped into the stent pattern, the wax is again liquefied and removed from the lumen 103. Vacuum or pressure assistance, or a solvent, may be used to assist in draining the liquefied wax from lumen 103. Further, the annealing process, as discussed above, may vaporize any residual wax remaining in the lumen 103.

Openings 104 are formed through the wall of hollow wire 102 to access lumen 103 and may assist in draining the fluid, depending on the fluid used. Thus, openings 104 may be formed before or after the step of draining the fluid from hollow wire 102. Lumen 103 is then filled with a drug, thereby providing a hollow, drug-eluting stent.

In another embodiment, lumen 103 is filled with the biologically or pharmacologically active substance prior to bending hollow wire 102. The biologically or pharmacologically active substance may be pressurized as described above with respect to FIGS. 17-18, but need not be. The biologically or pharmacologically active substance is densely packed into lumen 103, thereby providing support to hollow wire 102 as hollow wire 102 is formed into the stent pattern. In some applications, after forming the stent in the stent pattern, fusing selected crowns of the stent may adversely affect some biologically or pharmacologically active substances due to heat at the fusion site. In some embodiments, the crowns need not be attached to each other at all, thereby avoiding the issue. In other embodiments, the crowns can be attached by mechanical means, spring clips, interconnecting crowns, soldering, adhesives, brazing, sutures, rivets, clamps, micro machined interlocking surfaces or other connecting means known to those skilled in the art, some of which are shown in FIGS. 31-36.

In another embodiment shown in FIGS. 19-20, a spring element 280 is disposed within lumen 103 of hollow wire 102. Spring element 280 may be inserted into lumen 103 of hollow wire 102 or hollow wire 102 may be formed around spring element 280. Spring element 280 may be formed of flattened steel or other suitable materials. Spring element 280 supports hollow wire 102 while hollow wire 102 is shaped into a stent pattern. Alternatively, the spring element could be placed on the outside of the hollow wire. After shaping hollow wire 102 into a stent pattern, spring element 280 is pulled, as shown by the arrow in FIG. 20. Pulling spring element 280 causes spring element 280 to straighten, as indicated at 282, thereby simplifying its removal from lumen 103. After spring element 280 is removed, openings may be cut in hollow wire 102 to access lumen 103 and lumen 103 may be filled with a biologically or pharmacologically active substance, as explained above, resulting in a hollow wire drug-eluting stent.

In another embodiment shown in FIGS. 21-22, instead of supporting wire 102 with a supporting element in the lumen 103, an outer member 290 envelops wire 102. Outer member 290 may be softer than wire 102. For example, outer member 290 may be made from tantalum and hollow wire 102 may be made from MP35N. Outer member 290 may not be attached to hollow wire 102. Outer member 290 and hollow wire 102 are bent together into a stent pattern, such as a sinusoidal pattern. Outer member 290 may then be removed, for example, by the methods described in co-pending U.S. application Ser. No. 12/500,359, filed Jul. 9, 2009, which is incorporated herein in its entirety. By having outer member 290 on the outside of hollow wire 102, it may be easier to remove outer member 290 compared to a supporting member disposed in lumen 103. After outer member 290 is removed, the stent forming process is finalized as described above and lumen 103 is loaded with a biologically or pharmacologically active substance, resulting in a hollow drug-eluting stent.

In other embodiments, the lumen of the hollow wire may be filled with a filler material such as a gel, hydrogel, alcohol, silica or a polymer, shaped into a stent pattern, and then the filler material may be removed. The filler material may be removed after the wire is shaped into a stent pattern, by exposing the shaped wire to solvent or solution in which the filler material is soluble or reacts but the wire is not soluble or reacts to remove the filler material, which can then be drained from the lumen with the solvent or solution. Examples of solvents may be water or alcohol and examples of a solution would be an acidic or basic solution such as HCL, sulfuric, ammonia, etc. If alcohol is used as a filler material, it can simply evaporate from the lumen.

In another embodiment shown in FIGS. 23-25, a core wire including an outer member 2302 and a core or inner member 2304 is swaged, for example, in a press 2308 such that a force is directed in the direction of arrows 2306. In this embodiment, inner member 2304 is made from a material that is harder than the material of the outer member 2302. In a non-limiting example, outer member 2302 may be made from MP35N and inner member 2304 may be made from a molybdenum-rhenium alloy, which is approximately twice as hard as MP35N. Thus, when the core wire is swaged, outer member 2302 deforms into a generally elliptical shape, but inner member 2304 remains generally circular, as shown in FIG. 24. This provides a gap or lumen 2310 between outer member 2302 and inner member 2304, generally to one side of inner member 2304. The wire is then shaped into a stent pattern and openings 2312 are laser-cut through outer member 2302 to expose inner member 2304. The stent is then exposed to an etchant, for example, xenon difluoride, as described in co-pending U.S. application Ser. No. 12/500,359, filed Jul. 9, 2009, incorporated by reference herein in its entirety. In some instances, some of the openings 2312 may become clogged and therefore impede the etching process. In the present embodiment, with lumen 2310 running the length of the wire between outer member 2302 and 2304, if a hole 2312 becomes clogged, the etchant from an adjacent hole 2312 flows through lumen 2310, as depicted by arrows 2314, to etch inner member 2302 along the length of the wire.

Sheet Embodiment

Another method for forming a stent including hollow struts is described referring to FIGS. 26-30. In this embodiment, rather than forming the stent from a wire bent into a stent pattern, the stent pattern is cut into flat sheets, rolled into a tube, and welded to form a stent with hollow struts. As illustrated schematically in FIG. 26, a first sheet 402 and second sheet 404 sandwich a third sheet 406 therebetween. First and second sheets 402, 404 are made from materials that form a finished stent, such as stainless steel, nitinol, MP35N, etc. Third sheet 406 is made from a material that can be removed from between first and second sheets 402, 404 after forming. For example, the materials described in co-pending U.S. application Ser. No. 12/500,359, filed Jul. 9, 2009 and incorporated by reference herein, for the outer member can be used for first and second sheets 402, 404, and the materials described therein for the sacrificial or core member can be used as third sheet 406. In a non-limiting example, first and second sheets 402, 404 are formed from MP35N and third sheet 406 is formed from tantalum.

With sheets 402, 404, 406 stacked, a flat stent pattern is stamped out of the sheets, as shown in FIG. 27. The stamping device cuts through sheets 402, 404, 406, leaving struts 407 of the flat stent pattern. The stamping device has curved edges that push third sheet 406 inward and first and second sheets 402, 404 together at edges 408, as shown in the cross-sectional view of struts 407 in FIG. 28. Openings 104 may be laser cut through strut 407 to reach the remaining material of sheet 406. The remaining material of sheet 406 can be removed by the methods described herein or in co-pending application Ser. No. 12/500,359, for example, using xenon difluoride gas. After the remaining material of sheet 406 is removed, the flat stent is rolled such that edges 410, 412 abut each other, and edges 410, 412 are bonded to each other, for example by a weld 414 as shown in FIG. 29. A cross-sectional view of the struts 407 of FIG. 29 is shown in FIG. 30, with hole 104 accessing lumen 103. The stent can then be filled with a biologically or pharmacologically active substance through openings 104 and/or additional openings drilled for the purpose of filling the stent. Those of ordinary skill in the art would recognize that the step of removing the remaining material of third sheet 406 may be performed before or after the flat stent is rolled and edges 410, 412 are welded to each other.

Examples of biologically or pharmacologically active substance that may be used to fill the lumen of the stents described above are listed in co-pending U.S. application Ser. No. 12/500,359, filed Jul. 9, 2009, which is incorporated by reference herein in its entirety. The term "biologically or pharmacologically active substance" refers to any substance, whether synthetic or natural, that has a pharmacological, chemical, or biological effect on the body or a portion thereof. Suitable biologically or pharmacologically active materials that can be used in embodiments of the present invention include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine, doxazosin, and sirolimus (rapamycin) or other—limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

Further, due to the relatively large volume of the biologically or pharmacologically active substance that can be carried by a hollow stent, such stent may be particularly useful for delivering chemotherapy or radiation therapy directly to a target location.

The step of filling lumen 103 with biologically or pharmacologically active substances 112, and other steps in processing the stent, such as cleaning, may be accomplished by the methods described in co-pending U.S. application Ser. Nos. 12/884,503; 12/884,578; 12/884,362; 12/884,451; 12/884,596; and 12/884,501, each of which is incorporated by reference herein in its entirety, or any other suitable methods known to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of forming a stent with hollow struts comprising the steps of:
   stacking a first sheet of a first material, a second sheet of a second material, and a third sheet of third material disposed between the first sheet and the second sheet to form a stacked laminate of materials;
   stamping a flat stent pattern from the stacked laminate of materials, wherein the stamping step removes the first, second, and third materials from portions of the stacked laminate of materials, thereby leaving the flat stent pattern with a cross-section having the first material, the second material, and the third material, wherein the stamping step pushes the third sheet inward and edges of the first sheet and the second sheet together to surround the third sheet such that a cross-section through struts of the flat stent pattern includes the first material and the second material completely surrounding the third material;
   after the stamping step, processing the stent pattern to remove the third material from within the first material and the second material such that a cross-section of the struts includes the first material and the second material surrounding a lumen;
   rolling the flat stent pattern such that longitudinal edges of the flat stent pattern abut against each other to form a tube, and bonding the longitudinal edges to each other; and
   filling the lumen with a biologically or pharmacologically active substance.

2. The method of claim 1, further comprising the step of forming openings through the first material or the second material from an outer surface of the first material or the second material through an inner surface of the first material or the second material.

3. The method of claim 2, wherein the step of forming openings is performed prior to removing the third material from within the first material and the second material.

4. The method of claim 2, wherein the step of forming openings is performed after removing the third material from within the first material and the second material.

5. The method of claim 1, wherein the step of rolling the flat stent pattern is performed after the step of processing the stent pattern to remove the third material.

6. The method of claim 1, wherein the step of rolling the flat stent pattern is performed before the step of processing the stent pattern to remove the third material.

7. The method of claim 1, wherein the first material and the second material are the same material.

8. The method of claim 7, wherein the first material and the second material are MP35N.

9. The method of claim 1, wherein the step of removing the third material comprises exposing the stent pattern to an etchant that removes the third material and does not adversely affect the first material and the second material.

10. The method of claim 9, wherein the etchant is xenon difluoride gas.

11. The method of claim 9, wherein the first material and the second material are both MP35N, the third material is tantalum, and the etchant is xenon difluoride gas.

12. The method of claim 1, wherein the step of processing the stent pattern to remove the third material is selected from the group consisting of chemical etching, wet chemical dissolution, solubilization, sublimation, and melting.

13. The method of claim 1, wherein the biologically or pharmacologically active substance is selected from the group consisting of glucocorticoids, antithrombotic agents, growth factors, antisense agents, anti-cancer agents, antiproliferative agents, oligonucleotides, antibiotics, antiplatelet agents, anti-coagulant agents, antimitotic agents, antioxidants, antimetabolite agents, and anti-inflammatory agents.

\* \* \* \* \*